United States Patent [19]

Findeisen

[11] 4,189,580
[45] Feb. 19, 1980

[54] PROCESS FOR THE PREPARATION OF NITRILES

[75] Inventor: Kurt Findeisen, Odenthal, Fed. Rep. of Germany

[73] Assignee: Bayer Aktiengesellschaft, Leverkusen, Fed. Rep. of Germany

[21] Appl. No.: 932,599

[22] Filed: Aug. 10, 1978

[30] Foreign Application Priority Data

Aug. 18, 1977 [DE] Fed. Rep. of Germany ....... 2737210

[51] Int. Cl.² .............................................. C07C 20/00
[52] U.S. Cl. .................................. 544/301; 260/346.3; 260/359; 260/464; 260/465 B; 260/465.2; 544/334; 544/356
[58] Field of Search ................. 260/464, 465 B, 465.2, 260/329 R, 346.3, 359; 544/301, 334, 356

[56] References Cited

U.S. PATENT DOCUMENTS

| | | | |
|---|---|---|---|
| 2,800,496 | 7/1957 | Toland, Jr. | 260/465 B |
| 3,012,059 | 12/1961 | Bezman | 260/465 B |
| 3,131,209 | 4/1964 | King | 260/465 B |
| 3,341,566 | 9/1967 | Nakaoka et al. | 260/465 B |
| 3,457,293 | 7/1969 | Sonobe et al. | 260/465 B |

*Primary Examiner*—Dolph H. Torrence
*Attorney, Agent, or Firm*—Sprung, Felfe, Horn, Lynch & Kramer

[57] ABSTRACT

A process for the preparation of a nitrile of the formula $$R-(CN)_{n'}$$

wherein R represents an optionally substituted alkyl, cycloalkyl or aryl radical or an optionally substituted 5- or 6-membered heterocyclic radical which may additionally be fused with a benzene ring and n' represents 1 to 6 which comprises contacting a carboxylic acid of the formula $$R-(COOH)_{n'}$$

wherein R and n' have the meanings given above with cyanogen chloride and/or cyanogen bromide at a temperature in the range of 100° to 300° C.

8 Claims, No Drawings

PROCESS FOR THE PREPARATION OF NITRILES

The invention relates to a process for the preparation of nitriles by reacting carboxylic acids with cyanogen chloride and/or cyanogen bromide.

A large number of methods are known for the preparation of nitriles. It is possible to obtain nitriles for example by
the addition of HCN to C≡C double bonds,
the addition of HCN to C≡O double bonds,
the addition of HCN to C≡N double bonds,
the reaction of alkyl mineral acid esters with metal cyanides, the condensation of aromatic diazonium salts with metal cyanides (Sandmeyer reaction), the condensation of cyanohalogens with Grignard compounds, Friedel-Crafts reactions of aromatic compounds with dicyanogen, the dehydrogenation of amines, the elimination of water from aldoximes, the elimination of water from amides, the action of ferrocyanide compounds or copper cyanide at elevated temperatures on aromatic halogen compounds, the reaction of ethers with HCN or cyanides (Houben-Weyl, Methoden der organischen Chemie (Methods of Organic Chemistry), 4th edition, Vol. VIII, page 335–338).

The preparation of nitriles from carboxylic acids is also described in detail in literature (Houben Weyl, Methoden der organischen Chemie, 4th edition, Vol. VIII, page 335–338).

The preparation of nitriles by the elimination of water from carboxylic acids can be conducted either using chemical means or by thermal methods. Both methods are associated with a number of disadvantages and have not been very widely used in preparative chemistry.

Thus although the ammonium salts of organic acids are converted, using water-elimination agents (phosphorous pentoxide, glycerol), into nitrile in a heterogenous reaction in order to obtain good yields, it is necessary to first of all synthesize the amide (Comp. rend. 25,383 (1847) and Ber. 19, 2459 (1886).

Although nitriles are also obtained by melting acids with potassium thiocyanate or lead thiocyanate, the best yields are obtained if instead of the acids their zinc salts are used. This method is time-consuming and thus uneconomical because of the lengthy preparation and drying of these salts (J. Amer. Chem. Soc. 38, 2120 (1916)). Higher molecular fatty acids or dicarboxylic acids are converted into nitrile when heated with urea or cyanuric acid to temperatures of 250° to 310° C., but the yields are low. They vary between 32% and 49% (Org. Synth. 25, 95 (1949)).

A process for the preparation of aromatic nitriles is known from J. Chem. Soc. 1946, 763, based on the reaction of aromatic acids with aryl sulphamides in the presence of phosphorous pentachloride or by heating to temperatures of over 200° C. Both process variations give very different yields (between 11 and 83%). What is disadvantageous in this process is that per mol of nitrile 1 mol of p-toluene sulphonyl chloride is formed, if phosphorous pentachloride, a substance which is very difficult to work with, is used as the condensation agent. In the condensation at above 200° C. one mol of p-toluene sulphonic acid and 1 mol of the ammonium salt of the p-toluene sulphonic acid are obtained per mol of nitrile.

Nitriles can also be prepared directly from organic acids catalytically using ammonia by means of thermal dehydration. However, the high temperatures required of 300° to 500° C. restrict this method to carboxylic acids and nitriles which are particularly resistant to heat. (for example J. Amer. Chem. Soc. 38,2128 (1916)).

A further process for the preparation of nitriles was described in U.S. Pat No. 2,377,795. From low-molecular nitriles which are used in a large excess nitriles form in the presence of an acid, the nitriles corresponding to the acids. The disadvantages of this process are the high temperatures and the use of a silver-plated autoclave as well as the industrially unsatisfactory yields and the use of low-boiling nitriles, which have to first of all be synthesized. Furthermore, this process seems to be restricted to the preparation of adipic acid dinitrile.

A process was found for the preparation of nitriles of the formula $$R-(CN)_{n'} \qquad (I)$$

in which
R represents an optionally substituted alkyl, cycloalkyl or aryl radical or for an optionally substituted 5- or 6-membered hetero-cyclic radical, which can additionally be fused with a benzene ring and
n' represents 1 to 6, characterised in that carboxylic acids of the formula $$R-(COOH)_{n'} \qquad (II)$$

in which R and n' have the above-mentioned meaning, are reacted with cyanogen chloride and/or cyanogen bromide at temperatures in the range of 100° to 300° C.

Preferably, in the case of the process according the invention, carboxylic acids of the formula (II) are used with n' representing 1 to 3. Alkyl radicals with up to 24 carbon atoms, preferably with up to 18 carbon atoms, which can optionally be substituted by chlorine, bromine, or methoxy, alkoxy-, nitrilo-, methoxycarbonyl- or ethoxycarbonyl-groups may represent the radical R in the above-mentioned formulae. The following optionally substituted alkyl radicals may for example be mentioned: methyl-, ethyl-, propyl-, butyl-, pentyl-, hexyl-, heptyl-, 2-ethylhexyl-, dodecyl-, tetradecyl-, hexadecyl-, octadecyl-, -chloro-propyl-, pivaloyl-, oleyl-, cyanmethyl-, 3-bromopropyl-, ω-methoxy-hexyl-, ω-ethoxyhexyl-, ω-methoxycarbonyl-butyl- and ω-ethoxycarbonyl-butyl-.

Further, the radical R can represent cycloalkyl radicals with up to 10 carbon atoms, preferably with up to 6-carbon atoms, which can be substituted by chlorine, bromine or methoxy-, ethoxy-, nitrilo-, methoxycarbonyl-, ethoxycarbonyl-, methyl-, ethyl-, propyl- or isopropyl-groups, or also for arylradicals, with up to 14 carbon atoms, preferably with up to 10 carbon atoms, optionally substituted by chlorine, bromine, nitro, or methoxy, ethoxy-, nitrilo-, methoxycarbonyl-, ethoxycarbonyl-, methyl-, ethyl-, propyl-, isopropyl- or tert.-butyl-groups. Examples which may be mentioned of optionally substituted cycloalkyl radicals are:
2-methyl-cyclohexyl-, 4-ethyl-cyclohexyl-2-chlorocyclohexyl- and 4-methoxycarbonyl-cyclohexyl-, and of optionally substituted aryl radicals: o-, m-, p-chlorophenyl-, 2,3-dichlorophenyl-, 3,4-dichlorophenyl-, 4-chloro-3-nitrophenyl-, 2-chloro-4-nitrophenyl-, 2-chloro-5-nitrophenyl-, 3,4- and 3,5-dinitrophenyl-, o-, m-, or p-tolyl-, 3-methyl-4-nitrophenyl-, 4-tert.-butyl phenyl-4-methoxycarbonyl-phenyl o-, m-, p-bromophenyl- and 4-ethoxycarbonyl-phenyl-radicals.

The following may be mentioned as the 5- or 6-membered heterocyclic radicals with up to 9 carbon atoms, preferably with up to 5 carbon atoms, optionally substituted with methyl-, ethyl-, chloro-, bromo-, nitro-, methoxycarbonyl-, ethoxycarbonyl-, or nitrile, which radical may be additionally fused with a benzene ring: 2,4,6-trioxopyrimidyl-, 2,4,6-trichloro-pyrimidyl-, dichloroquinoxalinyl-, thiophenyl as well as the phthalic anhydride and hexahydrophthalic anhydride radicals.

Preferably the following carboxylic acids of the formula (II) are used in the process according to the invention: acetic acid, propionic acid, butyric acid, valeric acid, hexanoic acid, heptanoic acid, 2-ethyl hexanol carboxylic acid, dodecanic acid, tetradecanic acid, hexadecanic acid, octadecanic acid, 3-chloroproponic acid, pivalic acid, 10-undecanic acid, oleic acid, sorbic acid, cyanoacetic acid, succinic acid, glutaric acid, adipic acid, sebacic acid, dodecane diacid, cyclohexan carboxylic acid, 3-cyclohexene-1-carboxylic acid, benzoic acid, o,m,p-chlorobenzoic acid, dichlorobenzoic acid, o, m, p-nitrobenzoic acid, 4-chloro-3-nitrobenzoic acid, 2-chloro-5-nitro-benzoic -acid, 2-chloro-4-nitrobenzoic acid, 3,4- and 3,5-dinitrobenzoic acid, phenylacetic acid, o-, m-, p-toluic acid, 3-methyl-4-nitrobenzoic acid, 4-tert-butyl benzoic acid, naphthalene carboxylic acid, 4'-nitro-bis-phenyl-4-carboxylic acid, isophthalic acid, 4-chloroisophthalic acid, 4-nitroisophthalic acid, terephthalic acid, nitroterephthalic acid, chloroterephthalic acid, dichloroterephthalic acid, trimesic acid, anisic acid, 3-nitroanisic acid, 4,4'-oxybisbenzoic acid, 2,4'carbonyl bisbenzoic acid, 3-chloroanthraquinone carboxylic acid and 4,4'-carbonyl bisbenzoic acid.

The aromatic carboxylic acids mentioned are particularly preferred.

The reaction of the carboxylic acids of formula (II) with cyanogen chloride and/or cyanogen bromide, preferably with cyanogen chloride, may be conducted in the presence of solvents or diluents. As solvent or diluent all inert organic solvents may be used which do not enter into a chemical reaction with either the carboxylic acids or the cyanogen halide. Such solvents or diluents are for example o, m, p-xylenes, chlorbenzene, o-dichlorobenzene, the 1,2,3-, 1,2,4-, 1,2,5-, or 1,3,5-trichlorobenzenes, nitrobenzene, tetramethylene sulphone, N-methylpyrrolidone and hexamethylphosphoric-acid-triamide. As the solvent or the diluent the end product, carboxylic acid nitrile, may also be used and in many cases successfully. The solvents or diluents may be used alone or in a mixture with each other.

The quantity of the solvent or diluent added is in general 1 to 10% times, preferably 1 to 5% times, the amount of carboxylic acid used.

The reaction temperature may be varied within a large range. In general the process is conducted at temperatures in the range of 100° C. to 300° C., preferably in the range of 150° C. to 250° C. The reactants, carboxylic acid and cyanogen halide, are in general reacted in a ratio of approx. 1:1. If the cyanogen halide is used in excess, this factor is of no significance to the reaction.

The reaction is in general conducted under normal pressure. When using low boiling, aliphatic carboxylic acids a slight excess pressure is desirable to achieve the reaction temperature. The reaction pressure is in general approx. 1 to 10, preferably 1 to 5 mm Hg.

By adding catalytic amounts of Lewis acids (approx. 0.001 to 0.1 mol, preferably 0.01 to 0.05 mol) the reaction can be accelerated. Suitable Lewis acids which can for example be mentioned are zinc-II-chloride, zinc cyanide, iron-(III)-chloride, tin-(IV)-chloride, aluminum chloride and boron trifluoride.

According to the process of the invention nitriles of the formula (I) can be obtained in good yields and high purities. Apart from hydrogen chloride and carbon dioxide no secondary products are formed. Of particular industrial significance is the general applicability of the process of the invention. It is not restricted to particular carboxylic acids. The working up of the reaction mixture does not present any problems since the reaction products are obtained in many cases in such a pure form that a purification process is not required.

A further advantage is that the starting products, i.e. the carboxylic acids as well as cyanogen chloride and cyanogen bromide are easily accessible technically. If the products are not available in large quantities they can easily be synthesized according to known methods.

The nitriles according to the invention are valuable intermediary products for the synthesis of dyes, such as azo dyes, polyisocyanates or polyamides (Polyurethanes, Chemistry and Technology, Saunders-Frisch, Interscience Publishers, New York, London, Vol. I and II, 1962).

The process according to the invention may be illustrated with the aid of the following examples, without the process being however limited to the examples.

EXAMPLE 1

In a three-necked flask 122 g benzoic acid (1 mol) are heated to 180°–200° C. and after 1 g zinc chloride has been added 61 g (51 ml) cyanogen chloride (cyanogen bromide can also be used instead of cyanogen chloride) are introduced dropwise over 60 minutes. $CO_2$ and HCl begin to evolve rapidly. The cyanogen chloride is separated from the gases by intensive cooling and drops back into the reaction vessel. After the cyanogen chloride has been consumed distillation is conducted.

Yield: 95 g benzonitrile (92% of theory), $bp_{15}$: 76°–78° C.

As described in Example 1 the following acids were converted into their nitriles with cyanogen chloride:

| | nitriles |
|---|---|
| p-methyl-benzoic acid | (89% of theory, $b.p._{11}$:91° C.) |
| o-nitrobenzoic acid | (85% of theory, m.p.:108°–109° C.) |

EXAMPLE 2

144.2 g 2-ethylhexanoic acid (1 mol) are dissolved in 100 g 2-ethylhexanoic acid nitrile, reacted with 1 g zinc cyanide and heated to 190°–210° C. Within 3 hours 123 g cyanogen chloride (2 mols) are added dropwise. Following this addition stirring is continued for 15 minutes at the reaction temperature, and distillation is then conducted under vacuum.

Yield: 110 g 2-ethylhexanoic acid nitrile (88% of theory), $b.p._{10}$: 71°–73° C.

100 g 2-ethylhexanoic acid nitrile are recovered unchanged.

EXAMPLE 3

201 g 6-chloro-3-nitrobenzoic acid (1 mol) are melted and heated to 170°–190° C. and rapidly reacted dropwise with 92 g cyanogen chloride (1.5 mols). After approx. 40 minutes the reaction is complete and no more hydrogen chloride evolves. The reaction product is distilled by aid of an oil pump.

Yield: 175 g 6-chloro-3-nitrobenzonitrile (96% of theory).
b.p.: 160°–163° C./0.3 mm Hg.

EXAMPLE 4

146 g adipic acid (1 mol) are dissolved in 200 ml tetramethylene sulphone and reacted dropwise with 215 g cyanogen chloride (3.5 mols) in the presence of 1 g iron-III-chloride at approx. 200° C. After four hours the reaction is complete.

The reaction mixture is allowed to cool, is poured into water, the oily phase is separated off, the reaction mixture is then dried over sodium sulphate, the sodium sulphate is filtered off and the reaction mixture is then distilled.

Yield: 91 g adipic acid dinitrile (84% of theory), b.p.: 179°–182° C. at 20 mm Hg.

EXAMPLE 5

83 g isophthalic acid (0.5 mol) are added to 200 ml tetramethylene sulphone and heated to 210°–220° C. At this temperature 61.5 g cyanogen chloride (1 mol) are added dropwise within 2 hours, the mixture is stirred for a further 15 minutes, filtered, allowed to cool, poured into water and the reaction product precipitated is filtered.

Yield: 58 g isophthalic acid dinitrile (91% of theory), m.p.: 162° C. (from ethyl acetate).

EXAMPLE 6

As described in Example 5, the following acids are converted with cyanogen chloride into the di- or trinitriles:

|  | dinitriles |
|---|---|
| terephthalic acid | (95%, m.p.: 223° C.) |
| 5-nitroisophthalic acid | (98%, m.p.: 190° C.) |
| 4-chloroisophthalic acid | (96%, m.p.: 149° C.) |
| 2-chloro-terephthalic acid | (98%, m.p.: 156° C.) |
| benzene tricarboxylic acid-(1,3,5) | trinitrile (98%, m.p.: 254° C.) |

EXAMPLE 7

128 g cyclohexanoic carboxylic acid (1 mol) are heated to 180°–200° C., reacted with 1 g aluminium chloride and 123 g cyanogen chloride (2 mols) are added dropwise within 3 hours. After the evolution of $CO_2$ and HCl has ended, distillation takes place.

Yield: 94 g cyclohexylnitrile (86% of theory), b.p.: 68°–70° C. at 12 mm Hg.

What is claimed is:

1. A process for the preparation of a nitrile of the formula $$R-(CN)_{n'}$$

wherein R represents unsubstituted alkyl or substituted alkyl substituted by chlorine, bromine, methoxy, alkoxy, nitrilo, methoxycarbonyl, or ethoxycarbonyl, unsubstituted cycloalkyl or substituted cycloalkyl substituted by chlorine, bromine, methoxy, ethoxy, nitrilo, methoxycarbonyl, ethoxycarbonyl, methyl, ethyl, propyl or isopropyl, unsubstituted aryl radical or substituted aryl substituted by chlorine, bromine, nitro, methoxy, ethoxy, nitrilo, methoxycarbonyl, ethoxycarbonyl, methyl, ethyl, propyl, isopropyl or tert.-butyl or unsubstituted 5- or 6-membered heterocyclic radical or substituted 5- or 6-membered heterocyclic radical which may additionally be fused with a benzene ring where the substituents are methyl, ethyl, chloro, bromo, nitro, methoxycarbonyl, ethoxycarbonyl or nitrile and n' represents 1 to 6 which comprises contacting a carboxylic acid of the formula $$R-(COOH)_{n'}$$

wherein R and n' have the meanings given above with cyanogen chloride and/or cyanogen bromide at a temperature in the range of 100° to 300° C.

2. A process according to claim 1 wherein a carboxylic acid of the formula given in claim 1 is employed wherein
R represents substituted or unsubstituted alkyl radical with up to 18 carbon atoms, substituted or unsubstituted cycloalkyl radical with up to 6 carbon atoms or substituted or aryl unsubstituted radical with up to 10 carbons atoms or substituted or unsubstituted 5- or 6-membered heterocyclic radical with up to 5 carbon atoms which heterocyclic radical can additionally be fused with a benzene ring and n' represents 1 to 3.

3. A process according to claims 1 or 2 wherein the reaction is conducted in the presence of an inert organic solvent or diluent.

4. A process according to claim 3 wherein the inert solvent or diluent is o-, m-, or p-xylene, chlorobenzene, o-dichlorobenzene, 1,2,3-, 1,2,4-, 1,2,5-, 1,3,5-trichlorobenzene, nitrobenzene, tetramethylene sulphone, N-methylpyrrolidone or hexamethylphosphoric acid triamide.

5. A process according to claim 3 wherein the quantity of solvent or diluent employed is 1 to 10 times the amount of the carboxylic acid employed.

6. A process according to claim 1, wherein the reaction is conducted in the presence of a Lewis acid.

7. A process according to claim 6 wherein the Lewis acid is zinc-II-chloride, zinc-cyanide, iron-III-chloride, tin-IV-chloride, aluminum-chloride and/or boron trifluoride.

8. A process according to claim 6 wherein the Lewis acid is employed in an amount of 0.001 to 0.1 mol.

* * * * *